(12) United States Patent
Heitmeier et al.

(10) Patent No.: US 6,830,047 B2
(45) Date of Patent: Dec. 14, 2004

(54) ANAESTHETIC CONTROLLER

(75) Inventors: Rolf Heitmeier, Baunatal (DE); Gerhard Niessner, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 21 days.

(21) Appl. No.: 09/808,984

(22) Filed: Mar. 16, 2001

(65) Prior Publication Data

US 2001/0022182 A1 Sep. 20, 2001

(30) Foreign Application Priority Data

Mar. 17, 2000 (DE) ................................. 200 05 004 U

(51) Int. Cl.[7] .............................................. A61M 16/00
(52) U.S. Cl. ............................ 128/203.14; 128/203.12; 128/203.13; 128/203.25
(58) Field of Search ...................... 128/203.12, 203.13, 128/203.14, 203.25, 204.22, 204.18, 204.21, 204.23

(56) References Cited

U.S. PATENT DOCUMENTS

| | | | | |
|---|---|---|---|---|
| 4,917,080 A | * | 4/1990 | Bayerlein | 128/204.23 |
| 5,094,235 A | * | 3/1992 | Westenskow et al. | 128/203.12 |
| 5,649,531 A | * | 7/1997 | Heinonen | 128/203.12 |
| 5,699,788 A | * | 12/1997 | Lekholm et al. | 128/203.12 |
| 5,727,545 A | * | 3/1998 | Psaros | 128/203.12 |
| 5,771,882 A | * | 6/1998 | Psaros et al. | 128/200.14 |
| 5,806,513 A | * | 9/1998 | Tham et al. | 128/203.12 |
| 5,967,141 A | * | 10/1999 | Heinonen | 128/203.12 |

* cited by examiner

*Primary Examiner*—Glenn K. Dawson
*Assistant Examiner*—Darwin P Erezo
(74) *Attorney, Agent, or Firm*—Diller, Ramik & Wight

(57) ABSTRACT

For automatic supply of an active substance to a patient's body (14) the supply rate (R) of an infusion pump (13) is evaluated. The supply rate is processed in a patient model (11) which receives the corresponding active substance data from a drug data bank (12). The patient model (11) calculates the concentration ($CN_{actual}$) in the patient's body from the former values of the active substance supply. Said actual concentration value is fed to a concentration controller (17) which also receives a desired concentration value ($CN_{desired}$). The infusion pump (13) is controlled as a function of the difference obtained. The desired concentration value can be manually set on an input device (19) or is supplied by another control portion which generates e. g. a BIS level or an adequate signal from the patient's EEG, the BIS level being a measure of the depth of anaesthesia.

21 Claims, 1 Drawing Sheet

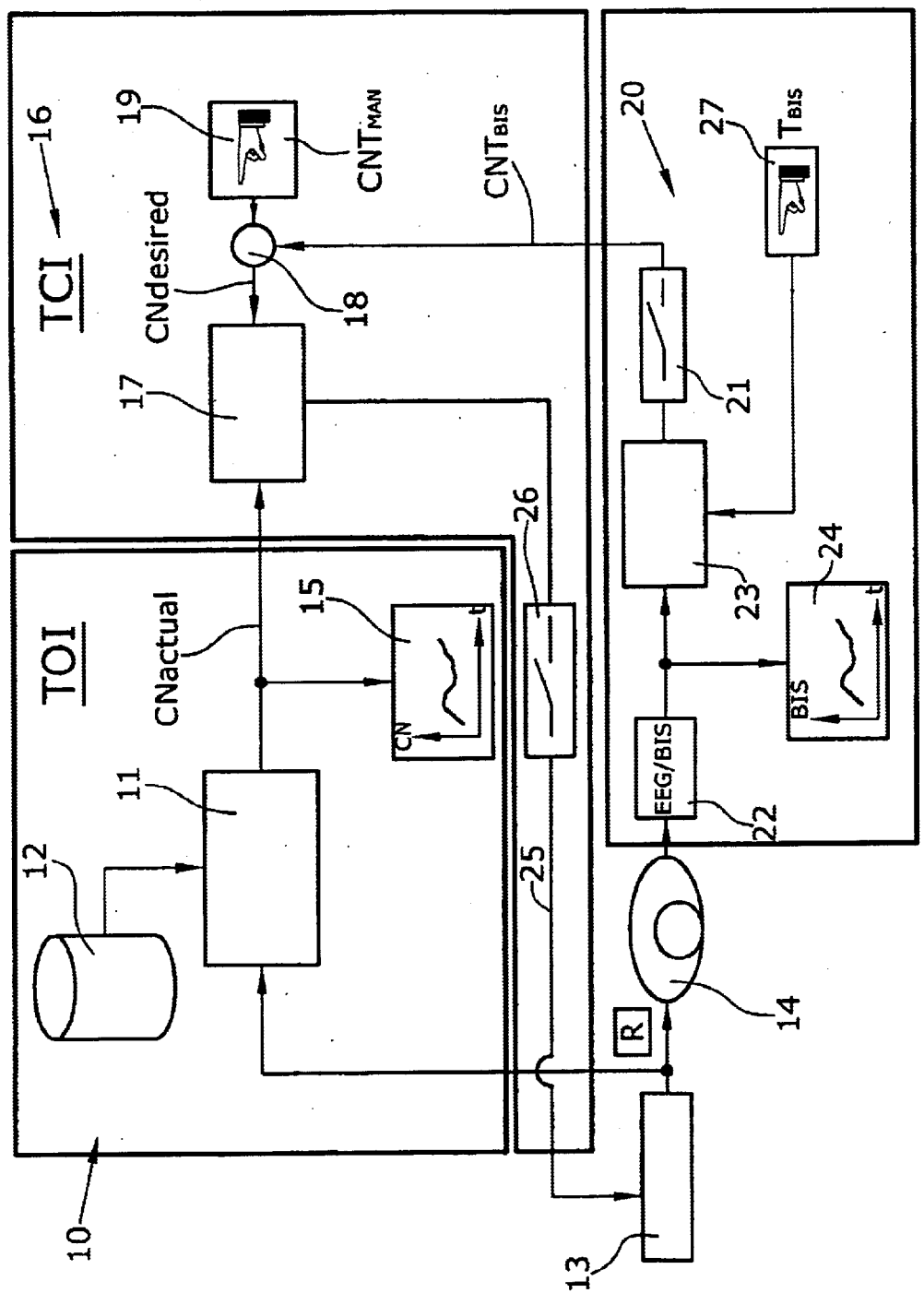

ANAESTHETIC CONTROLLER

BACKGROUND OF THE INVENTION

The invention relates to an anaesthetic controller for influencing the rate of active substance supply to a patient's body to attain and maintain a required state of anaesthesia.

For quite some time research work has been carried out with regard to closed-loop control systems for anaesthesia purposes. In the field of pharmaceutical research fundamental action models of specific active substances have been developed. The findings allow a mathematical simulation of the active substance concentration in the patient's blood plasma. The prediction accuracy is approximately ±30%. Latest applications allow a model-based control of specific active substances. According to the handling habits of the user it is desired to make use of the quality of predicting algorithms or the quality of directly controlling algorithms. An essential feature in this connection is the fundamental finding that an empirically determined model cannot simulate the entire correlations and the calculated concentration is not necessarily connected with the active effect and its intensity. In any case, a medical experience-based correction carried out by the user utilizing various non-measurable parameters for evaluating the intensity of the active effect is desirable.

SUMMARY OF THE INVENTION

It is an object of the invention to provide an anaesthetic controller operating on the basis of the active substance concentration in the patient's body although said active substance concentration is not detectable as a measured variable in real time.

According to the present invention the present active substance concentration in the patient's body is calculated on the basis of a patient model taking into consideration former active substance supply values. According to the current value of the present active substance concentration calculated in this way the active substance supply rate to the anaesthetic controller is changed such that the present active substance concentration is controlled to attain a target value. In this manner a closed-loop control system controls the active substance concentration in the patient's body such that a desired target value is attained. The patient model is operated on the basis of a predicting algorithm taking into consideration former active substance supplies, wherein it is possible to distinguish between different distribution periods with different time responses. The patient model thus delivers, on the basis of the preceding active substance rates and supply periods, information on the present active substance concentration in the patient's body. This calculation is of the predicting type and is termed TOI method (target-oriented infusion). The parameter set required for calculating the active substance concentration is taken from a drug data bank and transferred to the patient model. The patient model calculates the active substance concentration on the basis of the profile of the former active substance supply, wherein this value can be used as actual value for control purposes.

The target value of the active substance concentration can be adjusted by the user on an input device. This allows medical knowledge to be integrated in the control. The supervising physician can determine a target value on the basis of a time chart of the active substance concentration in the patient's body and adjust said target value. He can also carry out a time modification of said target value.

According to a preferred aspect of the invention the control portion for the active substance concentration is supplemented by a BIS control portion. The latter delivers a respective target value of the active substance concentration from the bispectral index. Said bispectral index is a characteristic value derived from the patient's EEG and indicates an anaesthestic level. The index ranges between values of 0 (wide awake) and 100 (sedated). On the basis of the respective BIS value the target value of the active substance concentration can be manually adjusted. However it is also possible to use the BIS value for automatic adjustment of the target value of the active substance concentration. Preferably the time behaviour of the BIS value is indicated on a display. The user can thus obtain at any time a complete representation of the active substance supply, the active substance concentration and the depth of anaesthesia.

BRIEF DESCRIPTION OF THE DRAWING

Hereunder an embodiment of the invention is explained in detail with reference to the only FIGURE of the drawing.

The drawing shows a block diagram of the anaesthestic controller.

BRIEF DESCRIPTION OF THE PREFERRED EMBODIMENT

The anaesthetic controller comprises a model computing portion 10 including a patient model 11. The patient model is a mathematical simulation of the reaction of the patient's body to active substances. The data of numerous active substances are included in a drug data bank 12. The patient model 11 is a complex model made up of three distribution rooms showing different time responses. The patient model is not only supplied with active substance data from the drug data bank 12 but also with data on the active substance concentration in the respective drug.

An infusion pump 13 delivers an infusion fluid containing the active substance at a supply rate R to the patient's body 14. The value of the supply rate R is continuously communicated to the patient model 11.

From the former values of the active substance supply the patient model 11 calculates the actual value of the active value concentration $CN_{actual}$ in the patient's body. At the same time said actual value of the active substance concentration $CN_{actual}$ over a period t is indicated on a display 15.

The active substance concentration in the patient's body is, in the present case, the active substance concentration in the patient's blood plasma, which is determined according to the predicting algorithm TOI (target-oriented infusion) from the supply rate R values.

The value $CN_{actual}$ is supplied to a concentration controller 17 included in a control portion 16. The concentration controller 17 further receives the desired value of the active substance concentration $CN_{desired}$ from a selection means 18. Said selection means 18 selects either the manually entered target signal $CNT_{MAN}$ of the active substance concentration delivered by an input means 19 or the signal $CNT_{BIS}$ delivered by a BIS control portion 20. Said signal is supplied via a switching means 21. When said switching means 21 is locked, signal $CNT_{MAN}$ is effective as desired signal $CN_{desired}$. When said switching means 21 is switched to passage only the signal $CNT_{BIS}$ is effective.

The BIS control portion 20 includes an EEG-BIS converter 22 which determines a BIS level from the EEG signals delivered by the patient's body 14, the BIS level being a measure of the depth of anaesthesia.

The BIS control portion 20 further includes a BIS controller 23 to which is supplied on the one hand a BIS target value $T_{BIS}$ as desired value and on the other hand the BIS signal from the EEG-BIS converter 22. The BIS controller 23 generates the target signal of the active substance concentration $CNT_{BIS}$ from the control deviation, i. e. the difference between the signals $T_{BIS}$ and BIS.

In the BIS control portion the BIS level over time t is indicated on a display 23.

In the control line 25 from the concentration controller 17 to the infusion pump 13 a switching means 26 is provided. When said switching means 26 is in the conducting state, the concentration controller 17 assumes control of the infusion pump 13. Said concentration controller can be operated according to current deterministic control methods, e. g. as PID-controller, two-position controller or similar.

According to the position of the switching means 21 the selection means 18 selects whether the signal $CNT_{BIS}$ or the signal $CNT_{MAN}$ is to be supplied as desired signal $CN_{desired}$. The user can thus either set a desired active substance concentration $CN_{MAN}$ at the input means 19 or a desired BIS level at an input device 27. When a BIS level is entered and the switching means 21 is in the conducting state, the capacity of the infusion pump 13 is controlled such that the desired BIS level $T_{BIS}$ is adhered to.

Combination of TCI control and BIS control offers the advantage that independently of the built-up bispectral index (BIS) rapid control of a first concentration level takes place. The user can obtain at any time a complete representation of the active substance supply, the plasma concentration and the depth of anaesthesia.

For monitoring automatic anaesthesia the therapeutic range of the active substance supply is supervised. For this purpose it is checked whether the active substance concentration remains between an upper and a lower limit value. If the limit values are reached, the user is informed accordingly so that he can take the necessary measures. Parallel to this the active substance consumption, which is an important parameter of anaesthesia, is monitored.

Although a preferred embodiment of the invention has been specifically illustrated and described herein, it is to be understood that minor variations may be made in the apparatus without deportioning from the spirit and scope of the invention, as defined in the appended claims.

What is claimed is:

1. An anaesthetic control system comprising:
   a) a patient model (11) created by former values of an active substance previously delivered to numerous other patients' bodies;
   b) means (13) for delivering the active substance at a present delivery rate (R) to a patient's body 914);
   c) means for continuously communicating the present delivery rate (R) to the patient model (11) which calculates a present active substance concentration ($CN_{actual}$) in the patient's body (14) under consideration of active substance values delivered to the actual patient during the running anaesthetic treatment;
   d) control means (17) for generating a control signal dependent upon the present active substance concentration ($CN_{actual}$) and a desired active substance concentration ($CN_{desired}$); and
   e) means (25) for conducting the generated control signal to the delivery means (13) for varying the present delivery rate (R) on a continuous basis as required to attain a deliver rate R) toward achieving the desired active substance concentration ($CN_{desired}$) in the patient's body (14).

2. The anaesthetic controller as defined in claim 1 wherein the former values (R) of the active substance supplied to the patient's body include prior active substance rates and prior active substance time periods of supply to the patient's body.

3. The anaesthetic controller as defined in claim 2 including means (19) for adjusting the target value ($CN_{desired}$) of the active substance concentration.

4. The anaesthetic controller as defined in claim 2 including means (20) for computing the target value ($CN_{desired}$) of the active substance concentration dependent upon patient's measured body functions.

5. The anaesthetic controller as defined in claim 2 including means (20) for computing the target value ($CN_{desired}$) of the active substance concentration dependent upon patient's measured body functions, and said computing means (20) includes means (23) for generating an active substance concentration target signal ($CNT_{BIS}$).

6. The anaesthetic controller as defined in claim 2 including means (20) for computing the target value ($CN_{desired}$) of the active substance concentration dependent upon patient's measured body functions, and said computing means (20) includes means (23) for generating an active substance concentration target signal ($CNT_{BIS}$) from a depth of patient's anaesthesia signal (EEG/BIS) and a BIS target value signal $T_{BIS}$.

7. The anaesthetic controller as defined in claim 2 including means (19) for generating a patient passive target signal ($CNT_{MAN}$) of the active substance concentration, means (20) for generating a patient dependent target signal ($CNT_{BIS}$) of the active substance concentration, and means (18) selectively responsive to said two last-mentioned means (19, 20) for transferring the desired value of the active substance concentration ($CN_{desired}$) to effect desired rate (R) of supply of the active substance to the patient's body.

8. The anaesthetic controller as defined in claim 2 including means (18) for selecting one of a patient passive target signal ($CNT_{MAN}$) of the active substance concentration and a patient dependent target signal ($CNT_{BIS}$) of the active substanceconcentration to effect desired rate (R) of supply of the active substance to the patient's body.

9. The anaesthetic controller 2 including means (18) for selecting between two separately generated active substance concentration target values ($CNT_{MAN}$, $CNT_{BIS}$) incident to effecting the desired rate (R) of supply of the active substance to the patient's body.

10. The anaesthetic controller as defined in claim 1 including means (19) for adjusting the target value ($CN_{desired}$) of the active substance concentration.

11. The anaesthetic controller as defined in claim 1 including means (20) for computing the target value ($CN_{desired}$) of the active substance concentration dependent upon patient's measured body functions.

12. The anaesthetic controller as defined in claim 1 including means (20) for computing the target value ($CN_{desired}$) of the active substance concentration dependent upon patient's measured body functions, and said computing means (20) includes means (23) for generating an active substance concentration target signal ($CNT_{BIS}$).

13. The anaesthetic controller as defined in claim 1 including means (20) for computing the target value ($CN_{desired}$) of the active substance concentration dependent upon patient's measured body functions, and said computing means (20) includes means (23) for generating an active substance concentration target signal ($CNT_{BIS}$) from a depth of patient's anaesthesia signal (EEG/BIS) and a BIS target value signal $T_{BIS}$.

14. The anaesthetic controller as defined in claim 1 including means (19) for generating a patient passive target signal ($CNT_{MAN}$) of the active substance concentration, means (20) for generating a patient dependent target signal ($CNT_{BIS}$) of the active substance concentration, and means (18) selectively responsive to said two last-mentioned means (19, 20) for transferring the desired value of the active substance concentration ($CN_{desired}$) to effect desired rate (R) of supply of the active substance to the patient's body.

15. The anaesthetic controller as defined in claim 1 including means (18) for selecting one of a patient passive target signal ($CNT_{MAN}$) of the active substance concentration and a patient dependent target signal ($CNT_{BIS}$) of the active substance concentration to effect desired rate (R) of supply of the active substance to the patient's body.

16. The anaesthetic controller as defined in 1 including means (18) for selecting between two separately generated active substance concentration target values ($CNT_{MAN}$, $CNT_{BIS}$) incident to effecting the desired rate (R) of supply of the active substance to the patient's body.

17. The anaesthetic controller as defined in claim 16 including means (19) for adjusting the target value ($CN_{desired}$) of the active substance concentration.

18. The anaesthetic controller as defined in claim 16 including means (20) for adjusting the target value ($CN_{desired}$) of the active substance concentration dependent upon patient's measured body functions.

19. The anaesthetic controller as defined in claim 1 including means (20) for computing the target value ($CN_{desired}$) of the active substance concentration dependent upon patient's measured body functions, and said computing means (20) includes means (23) for generating an active substance concentration target signal ($CNT_{BIS}$).

20. The anaesthetic controller as defined in claim 1 including means (20) for computing the target value ($CN_{desired}$) of the active substance concentration dependent upon patient's measured body functions, and said computing means (20) includes means (23) for generating an active substance concentration target signal ($CNT_{BIS}$) from a depth of patient's anaesthesia signal (EEG/BIS) and a BIS target value signal $T_{BIS}$.

21. The anaesthetic controller as defined in claim 16 including means (19) for generating a patient passive target signal ($CNT_{MAN}$) of the active substance concentration, means (20) for generating a patient dependent target signal ($CNT_{BIS}$) of the active substance concentration, and means (18) selectively responsive to said two last-mentioned means (19, 20) for transferring the desired value of the active substance concentration ($CN_{desired}$) to effect desired rate (R) of supply of the active substance to the patient's body.

* * * * *